United States Patent
Damato et al.

(10) Patent No.: US 8,931,960 B2
(45) Date of Patent: Jan. 13, 2015

(54) HIGH SPEED BALL BEARING FOR DENTAL OR MEDICAL HANDPIECES

(75) Inventors: Frank J. Damato, Keene, NH (US); Joseph P. Greathouse, Nelson, NH (US); Paul J. Carabello, Dublin, NH (US); Ryan D. Evans, North Canton, OH (US); Martin S. Galehouse, Muskegon, MI (US); Steven R. Morel, Swanzey, NH (US); John A. Zannotti, West Chesterfield, NH (US)

(73) Assignee: The Timken Company, North Canton, OH (US)

( * ) Notice: Subject to any disclaimer, the term of this patent is extended or adjusted under 35 U.S.C. 154(b) by 747 days.

(21) Appl. No.: 12/988,194

(22) PCT Filed: Apr. 17, 2009

(86) PCT No.: PCT/US2009/040907
§ 371 (c)(1),
(2), (4) Date: Nov. 24, 2010

(87) PCT Pub. No.: WO2009/129435
PCT Pub. Date: Oct. 22, 2009

(65) Prior Publication Data
US 2011/0059418 A1   Mar. 10, 2011

Related U.S. Application Data

(60) Provisional application No. 61/045,773, filed on Apr. 17, 2008, provisional application No. 61/122,624, filed on Dec. 15, 2008.

(51) Int. Cl.
*F16C 33/76*   (2006.01)
*A61C 1/00*    (2006.01)
(Continued)

(52) U.S. Cl.
CPC .............. *F16C 27/066* (2013.01); *A61C 1/181* (2013.01); *F16C 33/7846* (2013.01); *F16C 33/6633* (2013.01); *F16C 33/56* (2013.01); *F16C 33/58* (2013.01); *F16C 33/80* (2013.01)
USPC ......................................... 384/477; 433/114

(58) Field of Classification Search
USPC ................. 384/477, 480, 488, 515; 433/132; 415/904
See application file for complete search history.

(56) References Cited

U.S. PATENT DOCUMENTS 3,376,084 A    4/1968  McKee
4,623,590 A *  11/1986 Hodes et al. .................. 428/408
(Continued)

FOREIGN PATENT DOCUMENTS

DE   102006030836   1/2008
EP        0511105   10/1992
(Continued)

OTHER PUBLICATIONS

Machine translation of DE102006030836 A1.*
(Continued)

*Primary Examiner* — Thomas Diaz
(74) *Attorney, Agent, or Firm* — Michael Best & Friedrich LLP (57) ABSTRACT

A bearing assembly (20) for use in a medical, surgical, or dental handpiece (10) that enables spindle rotation for a supported rotary tool (36) at high speeds. The bearing assembly (28) incorporates annular gap shields (50, 54) at each axial end to prevent contaminate ingress and to retain lubricating grease within the bearing assembly (28) to avoid re-lubricated after each use or sterilization cycle.

21 Claims, 3 Drawing Sheets

(51) Int. Cl.
*A61C 1/18* (2006.01)
*F16C 27/06* (2006.01)
*F16C 33/78* (2006.01)
*F16C 33/66* (2006.01)
*F16C 33/56* (2006.01)
*F16C 33/58* (2006.01)
*F16C 33/80* (2006.01)

(56) References Cited

U.S. PATENT DOCUMENTS

| | | | | |
|---|---|---|---|---|
| 4,840,740 | A | * | 6/1989 | Sato et al. ............. 508/364 |
| 5,426,988 | A | * | 6/1995 | Ohata et al. ............. 74/55 |
| 5,918,986 | A | * | 7/1999 | Matsui et al. ............. 384/470 |
| 6,164,831 | A | * | 12/2000 | Matsui et al. ............. 384/469 |
| 6,402,158 | B1 | | 6/2002 | Imazaike |
| 2005/0130101 | A1 | * | 6/2005 | Novak et al. ............. 433/131 |
| 2006/0210948 | A1 | | 9/2006 | Rose et al. |

FOREIGN PATENT DOCUMENTS

| | | |
|---|---|---|
| EP | 0554773 A1 | 8/1993 |
| JP | 2003003184 | 1/2003 |
| WO | WO02/22039 | 3/2002 |

OTHER PUBLICATIONS

Machine translation of EP 05011105.*

International Search Report and Written Opinion for International Application No. PCT/US2009/040510 dated Jun. 29, 2009.
Annex I, Design Drawing submitted by Muller-Bore & Partner, in EP Application No. 09 732 417.2, Aug. 13, 2013, (1 page).
Annex II, Design Drawing submitted by Muller-Bore & Partner, in EP Application No. 09 732 417.2, Aug. 13, 2013 (1 page).
Reply to Written Opinion prepared by the EPO for EP Patent Appl. No. 09732417.2, dated Jan. 5, 2011, 5 pages.
Communication from the Examining Division for EP Patent Appl. No. 09732417.2 dated Mar. 22, 2012, 7 pages.
Reply to Communication from the Examining Division for EP Patent Appl. No. 09732417.2, dated Sep. 19, 2012, 13 pages.
Observations by Third Parties for EP Patent Appl. No. 09732417.2, dated Jul. 8, 2013, 12 pages.
English Translation of Observations by Third Parties for EP Patent Appl. No. 09732417.2, dated Aug. 13, 2013, 11 pages.
Letter from Patrick Craig Muldoon of Duane Morris to Mark E. Books of Polster, Lieder, Woodruff & Lucchesi dated Aug. 22, 2013, 7 pages.
Summons to Attend Oral Hearing for EP Patent Appl. No. 09732417.2, dated Sep. 26, 2013, 9 pages.
Letter with Amended Claims for EP Patent Appl. No. 09732417.2, dated Dec. 13, 2013, 9 pages.
Third Party Observations for EP Patent Appl. No. 09732417.2, dated Jan. 29, 2014, 12 pages.
European Intention to Grant Document for corresponding European Application No. 09732417.2, dated May 20, 2014, 27 pages.

* cited by examiner

HIGH SPEED BALL BEARING FOR DENTAL OR MEDICAL HANDPIECES

CROSS-REFERENCE TO RELATED APPLICATIONS

The present application is the U.S. National Stage under 35 U.S.C. §371 of International Application Ser. No. PCT/US2009/040907, having an International Filing Date of Apr. 17, 2009 and is related to, and claims priority from, U.S. Provisional Patent Application Ser. No. 61/045,773 filed on Apr. 17, 2008, and is further related to and claims priority from, from U.S. Provisional Patent Application Ser. No. 61/122,624 filed on Dec. 15, 2008, each of which are herein incorporated by reference.

STATEMENT REGARDING FEDERALLY SPONSORED RESEARCH

Not Applicable.

BACKGROUND OF THE INVENTION

This invention relates to medical, dental, and surgical handpieces, and in particular to a high-speed ball bearing for use in such handpieces.

Medical, dental, and surgical handpieces containing rotary tools supported on high-speed bearings are typically powered by an air turbine or electric motor. In either case, there are some common challenges to long bearing life. During operation, the bearings in such handpieces may be exposed to contamination in the form of both solid and liquid biological matter, as well as in the form of synthetic debris. The handpiece must be cleaned and sterilized between each patient. Typical cleaning and sterilization procedures require flushing of the head of the handpiece with solvents followed by high pressure steam sterilization in an autoclave system. Handpieces can reach temperatures ~134° C. in autoclaving processes. Both procedures are detrimental to the life of the bearings in that they degrade the properties of many lubricants and retainer materials, as well as remove the lubricant remaining in the bearings. In addition, the cleaning process requires that the head of the handpiece be disassembled so that any foreign matter can be removed from the handpiece head. This is time consuming and can be complicated. For this reason, cleaning of foreign matter (as opposed to sterilization) of medical, dental, and surgical handpieces may not be performed as often as is necessary.

In order to replenish the lubricant within the bearings, the user must inject oil into the drive system of the handpiece, operate the handpiece to expel excess oil and clean any oil residue from the exterior of the handpiece. In addition to the time and expense required to relubricate the handpiece, there is the unwanted added risk that excess lubrication can contaminate the working environment. Unwanted lubricant can be expelled within the handpiece body cavity during patient treatment and can contaminate the surface of the tooth or bone being treated, risking infection or resulting in poor adhesion of a amalgam or "filling" material, such as employed in dental procedures.

For medical, surgical, or dental handpieces having a rotary tool powered by an air driven turbine, air is discharged from exhaust vents located near the top and bottom of the of the handpiece head during use. This exhaust air may pass through the bearings on the way out of the head and accelerate the expulsion of lubricant from the handpiece. While the handpiece is slowing to a stop, the air flow physics of the handpiece are reversed. As the handpiece shuts down, the low pressure caused by the rotating turbine draws debris, into the head of the handpiece and the bearings within.

Accordingly, there is a need for an improved high-speed bearing suitable for application medical, surgical, or dental handpeices to provide support for rotary tools, and which is adapted for easy cleaning, exclusion of external contaminates, and which is configured to facilitate the retention of lubricants within the bearing assembly.

BRIEF SUMMARY OF THE INVENTION

Briefly stated, the present disclosure provides a bearing assembly for use in a medical, surgical, or dental handpiece that enables spindle rotation for a supported rotary tool at high speeds which may approach 500,000 rpm in dental handpieces. The bearing assembly incorporates annular gap shields at each axial end to prevent contaminate ingress and to retain lubricating grease within the bearing assembly to avoid re-lubrication after each use or sterilization cycle.

In one embodiment, the bearing assembly comprises an inner ring, an outer ring, a plurality of stainless steel or ceramic balls, and a retainer that separates the balls. The bearing assembly has an angular contact design, whereby one of the rings is relieved for assembly, and the retainer is a one-piece design which fully encompasses the equator of each ball. The retainer cannot be assembled into the bearing after the rings and balls are assembled, and the retainer is necessarily of a "non-crown" or "non-pronged" design. The bearing assembly further includes two shield closures, with the first shield preferably integral to the inner or outer ring, or non-integral and attached to the bearing in some other way. The first single shield is disposed to protect the interior of the bearing assembly from external debris and contaminates, with the shield directly adjacent to the exterior openings of the housing. The second shield, is mounted to either the inner or outer ring on either the ID or OD of the ring such that the original standard bearing chassis cross-section is not changed. The second shield is positioned between the interior of the bearing assembly (balls, retainer, and grease) and the driven member or rotary tool, without altering the external configuration of the bearing assembly. This second shield substantially encloses the annular gap between the inner and outer bearing rings, and prevents forced air that drives the turbine from driving lubricant out of the bearing assembly. The second shield also prevents ingress of cleaning solutions, foreign material, and contamination into the bearing that can compromise, degrade, dissolve, or otherwise remove the initial lubricant from the bearing. In non-air-turbine powered handpieces, the second shield encloses the interior of the bearing assembly more effectively than a single shield design, thus retaining factory-applied grease lubricant more effectively than prior art designs. The bearing can be sized for use in a variety of medical or dental handpiece applications.

In an embodiment of the present disclosure, the second shield component of the bearing assembly is a molded or machined component comprised of an engineering plastic (or polymer), composite or other material, such as an amorphous polyetherimide, with or without a glass filler. The second shield is capable of withstanding repeated sterilization, autoclaving, and exposure to associated high temperatures without degradation of mechanical properties, while maintaining a rigid barrier, and while preserving shield integrity.

In an embodiment of the present disclosure, the second shield component of the bearing assembly is configured as a "snap" shield, such that it will mechanically interlock with the inner bearing ring in an operational position, such as by snapping over a grove on the bearing ring outer diameter, or mechanically interlock with the outer bearing ring, such as by snapping into a groove on the bearing ring inner diameter. The "snap" mechanical interlocking approach eliminates the need for other fastening methods such as welding or affixing the shield with wire and provides for easy assembly. The shield is preferrably made of an engineering plastic material that will elastically deflect sufficiently during installation to permit a "snap" mechanical interlocking action which return the shield to an undeflected configuration when the shield is disposed at the operational position.

In an embodiment of the present disclosure, the retainer (cage) component of the bearing assembly is composed of an engineering plastic with a composition selected to withstand repeated sterilization and autoclaving procedures and temperatures without degradation of mechanical or tribological properties, similar to the second shield component.

In one embodiment, the retainer (cage) component of the bearing assembly is composed of a base material such as polyamide-imide (PAI), containing fillers including carbon (graphite or carbon fiber) present in amounts equal to, or greater than 10% of the component weight, and fluoropolymer particles in amounts equal to, or greater than, 1% of the component weight. The fluoropolymer particles may be polytetrafluoroethylene (PTFE, such as Teflon™). The presence of fillers enhance the tribological performance (low friction and wear) of the retainer.

In one embodiment, the retainer (cage) component of the bearing assembly is composed of a base material such as polyetheretherketone (PEEK), containing fillers including carbon (graphite or carbon fiber) present in amounts equal to, or greater than 10% of the component weight, and fluoropolymer particles in amounts equal to, or greater than, 5% of the component weight. The fluoropolymer particles may be polytetrafluoroethylene (PTFE, such as Teflon™).

The foregoing features, and advantages set forth in the present disclosure as well as presently preferred embodiments will become more apparent from the reading of the following description in connection with the accompanying drawings.

BRIEF DESCRIPTION OF THE SEVERAL VIEWS OF THE DRAWINGS

In the accompanying drawings which form part of the specification.

Corresponding reference numerals indicate corresponding parts throughout the several figures of the drawings. It is to be understood that the drawings are for illustrating the concepts set forth in the present disclosure and are not to scale. Before any embodiments of the invention are explained in detail, it is to be understood that the invention is not limited in its application to the details of construction and the arrangement of components set forth in the following description or illustrated in the drawings.

DETAILED DESCRIPTION

The following detailed description illustrates the invention by way of example and not by way of limitation. The description enables one skilled in the art to make and use the present disclosure, and describes several embodiments, adaptations, variations, alternatives, and uses of the present disclosure, including what is presently believed to be the best mode of carrying out the present disclosure.

Figure 1:
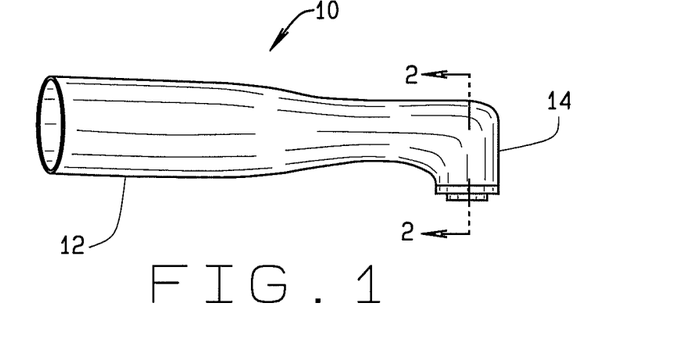
FIG. 1 is a perspective view of a medical, surgical, or dental handpiece.
Figure 2:
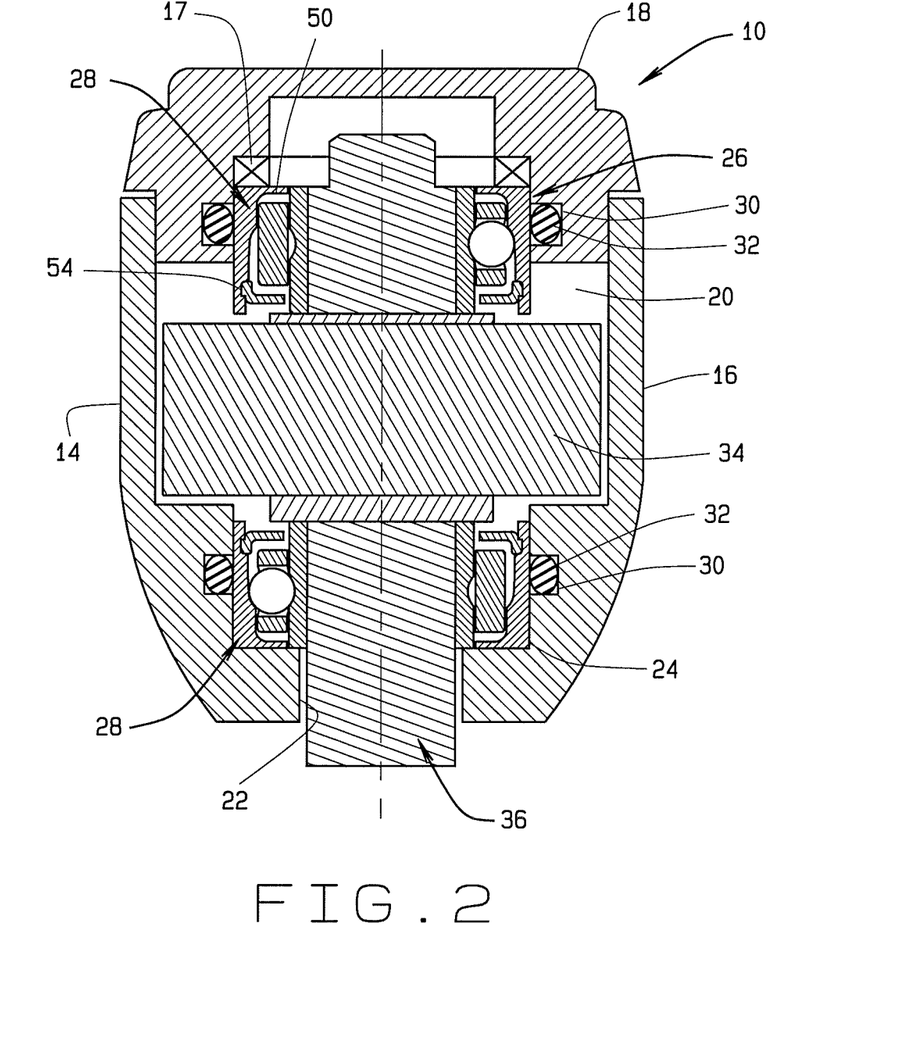
FIG. 2 is an enlarged cross-sectional view of a head of the handpiece shown in FIG. 1, incorporating a bearing assembly of the present disclosure.

Turning to the Figures, and to FIG. 1 in particular, powered hand-held instruments 10 (handpieces) for supporting rotary driven tools, that are used frequently in medical, surgical, or dental typically have a sleeve 12 and an end portion (or head) 14. As shown in FIG. 2, the head 14 comprises a body 16 and a cap 18 which, in combination, define an interior cavity 20. A bore 22 extends downwardly from the interior cavity 20 to the bottom of the head 14. The body 16 and cap 18 include aligned recesses 24 and 26, respectively, which each receive a bearing assembly 28. Circumferential channels 30 can be formed in the recesses 24, 26 to receive O-rings 32 which form seals around the outer circumference of each bearing assembly 28. A preload device 17 configured to exert an axial preload on each bearing assembly 28 is fitted in the recess 24, between the bearing assembly 28 and the cap 18.

In an air-driven handpiece, a driven member 34, such as a turbine or impeller as shown in FIG. 2, is received in the cavity 20. Correspondingly, for a motor-driven handpiece, the driven member 34 is a gear. The head 14 receives a spindle shaft 36, to which a rotary tool (or bit) can be attached, which extends through the head bore 22 into the cavity 20 to be received by each of the bearings 28 and engaged with the driven member 34 so that the driven member can rotationally drive the spindle and attached tool during use.

Figure 3:
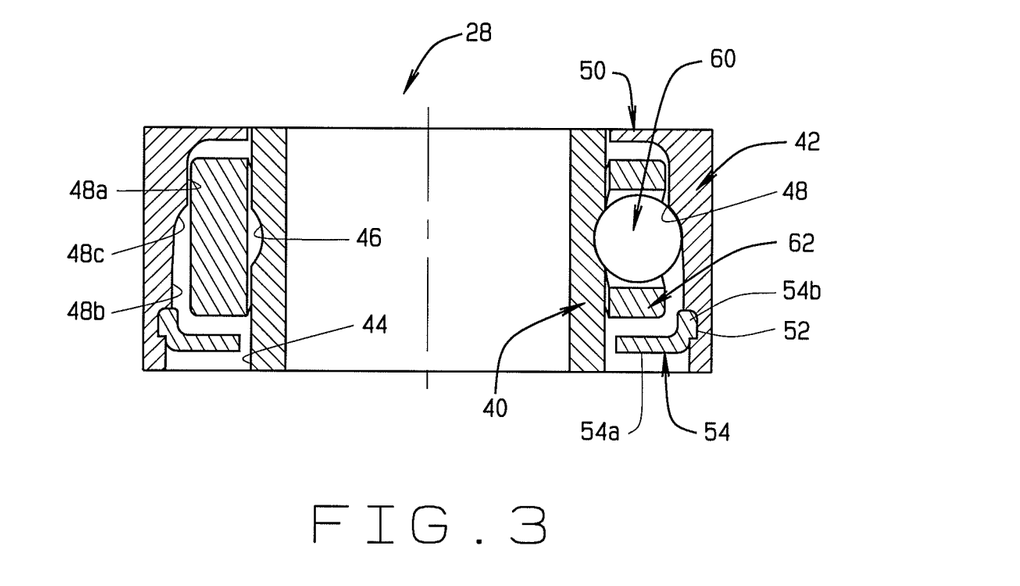
FIG. 3 is an enlarged cross-sectional view of the bearing assembly of the present disclosure.

Turning to FIG. 3, an illustrative bearing assembly 28 made in accordance with the present disclosure consists of an inner ring 40 and outer ring 42, both of which can be made of stainless steel. The inner ring 40 has an outer circumferential surface 44, with a curved or arcuate channel 46 formed in the surface 44. The curved channel 46 defines an inner raceway. The outer ring 42 has an inner circumferential surface 48 having a first portion 48a and a second portion 48b. The first and second portions 48a and 48b are both generally cylindrical, with the portion 48b having a larger diameter than the portion 48a. The two portions are joined by a curved or arcuate section 48c which defines an outer raceway.

The outer ring 42 further includes an integrated shield 50 at one axial end of the ring which extends radially inwardly toward the inner ring 40. The shield 50 has a length equal to at least 50% of the radial distance between the inner and outer rings. The radial distance between the inner and outer rings is defined as the difference between the outermost surface of the inner ring and innermost surface of the outer ring when the two rings are positioned coaxially. Preferably, the shield 50 extends substantially the full width of this radial distance to effectively close the axial end of the bearing assembly 28 without actually contacting the other ring during normal operation. That is, the shield 50 as defined in this disclosure is not a contact seal, such as an elastomeric lip seal which can be designed to contact and slide against a shaft.

A circumferential groove 52 is formed on the second portion 48b of the inner circumferential surface 48, proximate to the opposite axial end of the outer ring 42 from the integrated shield 50. A second shield 54 is received in the groove 52 to close the second axial end of the bearing assembly 28. The second shield 54 is generally L-shaped, and includes a radially inward extending leg 54a and an axially extending head portion 54b sized and shaped to be received in the circumferential groove 52. Preferably, the second shield 54 is a "snap" shield adapted to be snapped into place in the circumferential groove 52 as the shield head portion 54b mechanically interlocks with the groove 52. This mechanical interlocking as shown defines a "snap" shield design in this disclosure, and is will be understood to refer to a shield component which may elastically deform from an operating configuration or shape during installation, enabling the shield to be distorted from a rest configuration by the bearing ring component during installation, and to "snap" back to the rest configuration upon proper positioning adjacent the groove 52 The shield leg 54a is sized similarly to the first shield 50, and thus has a length equal to at least about 50% of the radial distance between the inner and outer rings, and preferably, has a length substantially the full width of this radial distance to close the second axial end of the bearing assembly 28. As with shield 50, the shield leg 54a effectively closes the axial end of the bearing assembly 28 without actually contacting the opposite ring during normal operation. That is, the shield 54 as defined in this disclosure is not a contact seal, such as an elastomeric lip seal which can be designed to contact and slide against a shaft.

As can be seen from FIG. 2, the shields 50 and 54 substantially close the opposite axial ends of each bearing assembly 28 contained within the head 14. The shields 50 and 54 are sized to allow clearance of the inner ring, and hence, although it is preferred that the shields extend at least about 50% of the width of the space between the inner and outer rings, and preferably as much of the distance as possible, the shields will not cover 100% of the annular gap between the inner and outer rings 40, 42. Although the second shield 54 is shown the be mounted to the inner circumferential surface of the outer ring 42, those of ordinary skill in the art will recognize that the second shield 54 could be mounted to the outer circumferential surface 44 of the inner ring 40 in substantially the same manner, without departing from the scope of the present disclosure.

The second shield 54 is made by molding or machining an engineering plastic, composite or other material that can withstand repeated sterilization, autoclaving, and application temperatures without degradation of mechanical properties. The engineering plastic, composite, or other material is selected to remain rigid and strong enough to function as a barrier to preserve shield integrity at any application or sterilization temperature which may be experienced by the handpiece 10 during normal usage. An example autoclaving sterilization temperature is ~134° C., and the preferred embodiment materials can accommodate this temperature level. The thermal expansion properties of the engineering plastic, composite, or other material are selected to ensure proper shield fit or retention occurs at any temperature within the normal operating range. One exemplary engineering plastic for forming the second shield 54 consists primarily of an amorphous polyetherimide, with or without glass filler, such as that sold under the registered trademark ULTEM containing no fillers.

Within the interior space of the bearing assembly 14, axially between the first and second shields 50, 54, a plurality of balls 60 are positioned within the curved channels 46 and 48c which define the inner and outer raceways. The curvatures of the raceways 46 and 48c each define a radius, with the radius of each being substantially the same, and as seen in FIG. 3, the curvature of the raceways corresponds substantially to the curvature of the balls 60. The curvature of the raceway 46 subtends an arc of between about 80° and about 90°, and preferably about 85°. The curvature of the raceway 48c, on the other hand, subtends an arc of between about 40° and about 50°, and preferably about 45°. The two arcs begin at approximately the same axial position. That is, one end of the arcs are the same distance from an axial end of the rings. The plurality of balls 60 are preferably formed from a ceramic such as silicon nitride ($Si_3N_4$) or steel, and are held in place between the raceways and relative to each other by a retainer or cage 62 having optimized dimensions and clearances for the intended operating conditions of the application.

The bearing assembly 28, including the balls 60, is preferably lubricated with a grease consisting of a mineral base oil and polyurea thickener. Nominal properties of a preferred grease or lubricant include a specific gravity of 0.9, a dropping point temperature of 470° F., a viscosity (cSt at 104° F.) of 110, penetration (unworked) of 195, and penetration (worked after 60 strokes) of 280. Those of ordinary skill will recognize that different greases or lubricants having desired properties may be utilized without departing from the scope of the present disclosure.

As seen in FIG. 3, the bearing assembly 28 has an angular contact design, whereby one of the rings is relieved for assembly and the one piece retainer or cage 62 is fitted that fully encompasses the equator of each ball. The retainer cannot be assembled into the bearing after the rings and balls are assembled, and the retainer is necessarily of the "non-crown" or "non-pronged" design.

As with the second shield 54, the retainer or cage 62 is designed to withstand repeated sterilization, autoclaving, and application temperatures without degradation of mechanical properties. The retainer can be made from an engineering plastic base material such as polyamide-imide (PAI), such as that sold under the registered trademark TORLON, or from polyetheretherketone (PEEK). In either case, the material preferably contains fillers, including carbon (graphite and or carbon fibers) and fluoropolymer particles such as polytetrafluoroethylene (PTFE, such as the trademarked TEFLON). The carbon filler is preferably present in amounts greater than or equal to about 10 wt %, while the fluoropolymer particle filler is preferably present in amounts greater than or equal to 1 wt % if the retainer is made from a PAI, or in amounts greater than or equal to about 5 wt % if the retainer is made from PEEK.

An exemplary composition of the retainer or cage 62 having a PAI base such as that sold under the registered trademark TORLON, consisting of about 20 wt. % carbon (graphite or fiber), about 3 wt. % fluoropolymer (such as polytetrafluoroethylene), and balance (about 77%) polyamide-imide-type polymer with respect to the total weight of the article.

An exemplary composition of the retainer or cage 62 having a PEEK base consists of about 15 wt. % PTFE, about 15 wt. % carbon fiber, and balance (70 wt. %) PEEK with respect to the total weight of the article.

The following table sets forth an example of nominal properties suitable for an embodiment of the second shield 54 and retainer 62:

| Property | Second "snap" shield | Retainer |
|---|---|---|
| General | | |
| Density (lb/in$^3$) | 0.046 | 0.054 |
| Water Absorption, 24 hrs | 0.25 | 0.33 |

-continued

| Property | Second "snap" shield | Retainer |
|---|---|---|
| (%) | | |
| Mechanical | | |
| Tensile Strength (psi) | 16,500 | 19,000 |
| Tensile Modulus (psi) | 475,000 | 1,130,000 |
| Flexural Strength (psi) | 20,000 | 30,200 |
| Flexural Modulus (psi) | 500,000 | 1,060,000 |
| Compressive Strength (psi) | 22,000 | 17,800 |
| Compressive Modulus (psi) | 480,000 | 580,000 |
| IZOD Notched Impact (ft-lb/in) | 0.5 | 1.6 |
| Thermal | | |
| Heat Deflection Temp (° F.) at 264 psi | 392 | 536 |
| Max Operating Temp (° F.) | 340 | 450 |

When assembled in the handpiece head 14, each bearing assembly 28 is oriented along the axis of the spindle shaft 36 such that the second shield 54 is positioned between the interior of the bearing assembly (including the balls 60, retainer 62, and internal grease) and the driven member 34. In an air powered device, the second shield 54 prevents air that drives the turbine from entering the bearing assembly and blowing grease out of the bearing assembly 28. The second shield 54 also prevents ingress of cleaning solutions, foreign material, and contamination into the bearing assembly 28 that can compromise, degrade, dissolve, or otherwise remove the initial lubricant from the bearing. In non-air-turbine powered handpieces, the second shield 54 encloses the interior of the bearing assembly 28 more effectively than prior single shield designs, thus retaining factory-applied grease lubricant more effectively than prior designs.

The second shield 54 works in combination with synergies achieved by retainer materials and grease specifications, as highlighted above. The synergies achieved by combining the three elements (i.e., a second shield, the retainer material, and grease selection) cooperatively function to extend the operational life of the bearing assemblies 28 when used in medical, surgical, or dental handpieces 10 subjected to repeated sterilization and autoclaving procedures. However, it is believed that some benefits could be realized by incorporating only a second shield; more benefits could be realized by incorporating the second shield and the retainer material; and the highest benefits could be achieved by incorporating all three elements (i.e., the second shield, the retainer material and the specified grease) as discussed above with respect to handpiece operation in the absence of periodic re-lubrication. Those of ordinary skill in the art will recognized that the bearing assemblies 28 of the present disclosure can be incorporated in older handpieces 10 as a retrofit option to dramatically improve performance of such older handpieces without redesigning the handpiece head 14.

Figure 4:
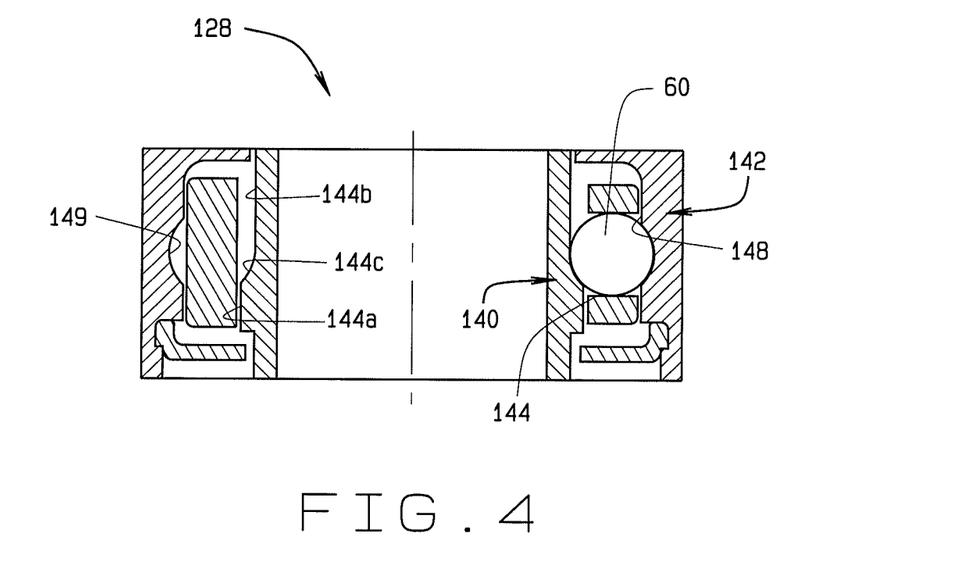
FIG. 4 is an enlarged cross-sectional view of an alternative embodiment of the bearing assembly of the present disclosure.

Turning to FIG. 4, and alternate embodiment 128 of the bearing assembly is shown. The bearing 128 is generally similar to bearing assembly 28 shown in FIG. 3, which can be described as an outer ring relieved design. In contrast, the bearing 128, as will become apparent from the description below, can be described as an inner ring relieved design. In this description of the bearing assembly 128, only the elements which are different from the corresponding elements in the bearing assembly 28 will be described.

The bearing assembly 128 comprises an inner ring 140 and outer ring 142 which can be made of stainless steel. The outer ring 142 has an inner circumferential surface 148 with a curved or arcuate channel 149 formed in the surface 148. The channel 149 defines an outer raceway. The inner ring 140 has an outer circumferential surface 144 having a first portion 144a and a second portion 144b. The first and second portions 144a and 144b are both generally cylindrical, with the portion 144a having a larger diameter than the portion 144b. The two portions are joined by a curved or arcuate section 144c which defines an inner raceway on the inner ring 140.

The curvatures of the raceways 149 and 144c each define a radius, with the radius of each being substantially the same, corresponding substantially to the curvature of the balls 60. The curvature of the raceway 144c subtends an arc of between about 45° and about 55°, and preferably about 50°. The curvature of the raceway 149, on the other hand, subtends an arc of between about 85° and about 95°, and preferably about 90°. The two arcs begin at approximately the same axial position. That is, one end of the arcs are the same distance from an axial end of the inner and outer rings 140, 142.

Like the bearing assembly 28, the bearing assembly 128 has an angular contact design, whereby one of the rings is relieved for assembly and the one piece retainer 62 is fitted that fully encompasses the equator of each ball 60. The difference is that in the bearing assembly 28, the outer ring is relieved and in the bearing assembly 128, the inner ring is relieved. In each embodiment, the retainer 62 cannot be assembled into the bearing assembly 28, 128 after the rings and balls are assembled, and the retainer 60 is necessarily of the "non-crown" or "non-pronged" design.

Figure 5:
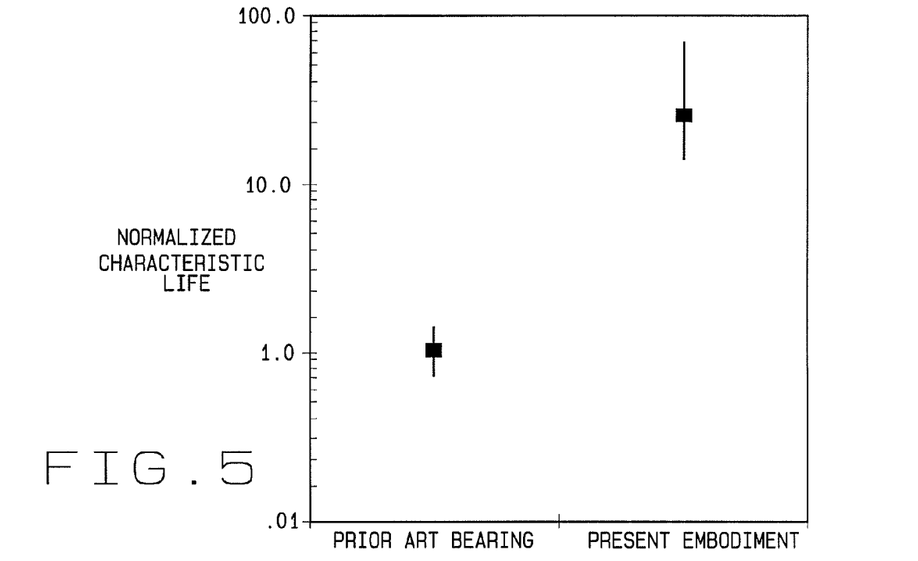
FIG. 5 is an exemplary graph illustrating a normalized life improvement of the bearing assembly of FIG. 3, as compared to a prior art bearing in the same handpiece under identical test conditions.

An exemplary test program was conducted to evaluate air turbine driven handpieces 10 incorporating the bearing assemblies 28 (i.e., containing a second shield enclosure 54) and other design modifications including new retainer material and grease options. The retainer 62 of the tested bearing 28 was comprised of about 15 wt. % PTFE, about 15 wt. % carbon fiber, and balance (about 70 wt. %) PEEK. The goal was for the bearing characteristic life to exceed 200 hours without additional lubrication in a handpiece test including a cyclic steam sterilization procedure. Prior art bearings were assembled and tested under identical conditions as the bearings 28. All test bearings passed a torque test prior to life testing. All test bearings were sterilized for 25 cycles in an autoclave at 134° C. prior to life testing. Handpieces 10 containing the test bearings were mounted in special testers with a simulated burr (pin or rotary tool) affixed to the head. Air pressure was first set to achieve a free running speed of 350,000 rpm (air pressure typically around 3 bar). A 170 g normal load was then applied to the simulated burr in a cyclic manner to simulate actual handpiece use by a dentist. After 50 load cycles, the sequence was paused for 30 seconds by shutting off the air pressure that drives the turbine 34 in the head 14. After the pause, another interval of load cycling began. After each 5,000 cycle period, technicians evaluated the condition of the test handpieces. Every 10,000 load cycles, each handpiece 10 was removed from the testers and sterilized for 10 cycles at 134° C. in an autoclave. The test was stopped once a handpiece 10 was unable to reach a free running speed of 280,000 rpm, was excessively loud, or had excessive run-out of the simulated burr. A 2-parameter Weibull approach was used to calculate characteristic lives of the test bearings. Results are shown in FIG. 5. Handpieces 10 incorporating prior art bearing assemblies were unable to meet the 200 hour test life goal, whereas handpieces 10 incorporating the bearing assembly 28 of the present invention surpassed the test goal and exceeded the prior art bearing assembly operational life by more than 10 times.

Figure 6:
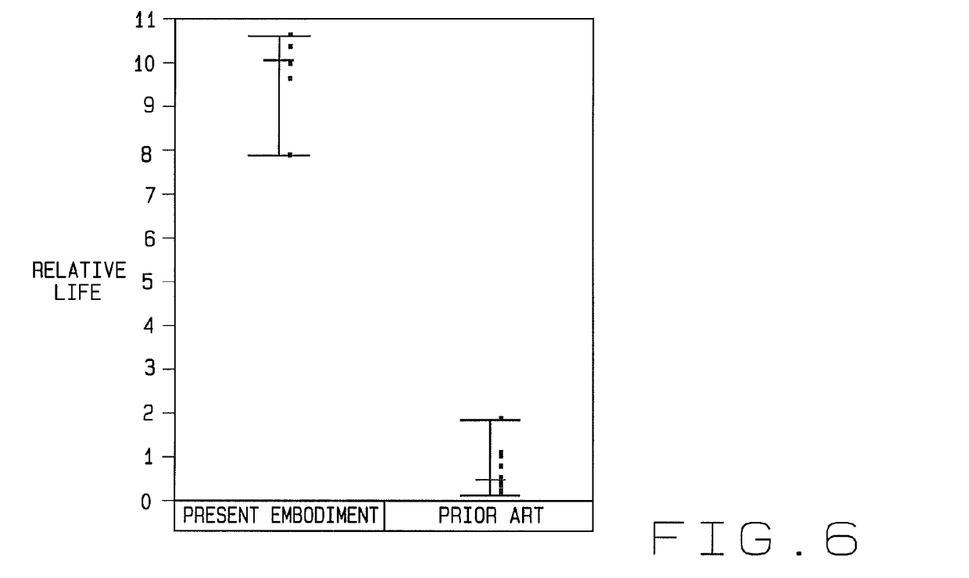
FIG. 6 is an exemplary graph comparing relative life improvement of the bearing assembly of FIG. 4, as compared to a prior art bearing in the same handpiece under identical test conditions.

A second test program was conducted to evaluate air turbine driven handpieces 10 incorporating the bearing assemblies 128 (i.e., containing a second shield enclosure) and other design modifications including new retainer material and grease options. The retainer 62 of the tested bearing 128 was comprised of a polyamide-imide (PAI) polymer, such as that sold under the name TORLON®, containing normally about 20% graphite and about 3% fluoropolymer fillers. The goal was for the bearing characteristic life to exceed 200 hours without additional lubrication in a handpiece test including a cyclic steam sterilization procedure. Handpieces 10 included prior art bearing assemblies were tested under identical conditions as handpieces 10 containing the bearing assemblies 128. All test bearings passed a torque test prior to life testing. All test bearings were sterilized for 25 cycles in an autoclave at 134° C. prior to life testing. Handpieces 10 containing the test bearings were mounted in special testers with a simulated burr (pin or rotary tool) affixed to the head. Air pressure was first set to achieve a free running speed of 350,000 rpm (air pressure typically around 3 bar). A 170 g normal load was then applied to the simulated burr in a cyclic manner to simulate actual handpiece 10 use by a dentist. After 50 load cycles, the sequence was paused for 30 seconds by shutting off the air pressure that drives the turbine 34 in the head 14. After the pause, another interval of load cycling began. After each 5,000 cycle period, technicians evaluated the condition of the test handpieces. Every 10,000 load cycles, the handpieces 10 were removed from the testers and sterilized for 10 cycles at 134° C. in an autoclave. The test was stopped once a handpiece 10 was unable to reach a free running speed of 280,000 rpm, was excessively loud, or had excessive run-out of the simulated burr. A 2-parameter Weibull approach was used to calculate characteristic lives of the test bearings. Results are shown in FIG. 6. Handpieces 10 incorporating the prior art bearing assemblies were unable to meet the 200 hour test life goal, whereas handpieces 10 incorporating the bearing assembly 128 surpassed the test goal and exceeded the prior art bearing life by approximately 10 times.

In view of the above, it will be seen that the present disclosure sets forth a bearing assembly 28, 128 for use in high-speed medical, surgical or dental handpieces 10 that can withstand routine autoclave steam sterilization (typically around temperatures of 134° C.) and requires no maintenance or re-lubrication during its extended useful life.

As various changes could be made in the above constructions without departing from the scope of the claimed invention, it is intended that all matter contained in the above description or shown in the accompanying drawings shall be interpreted as illustrative and not in a limiting sense. For example, although the first shield 50 is shown to be integral with the outer ring, the shield 50 could be integral with the inner ring. Alternatively, the shield 50 could be a snap fitted shield, similar to the second shield 54, which is snapped into place in the outer diameter surface of the inner ring, the inner diameter surface of the outer ring, or the outer diameter surface of the outer ring. The examples set forth herein, and the accompanying test results, are illustrative only, and do not limit the present disclosure to the specific features or properties set forth therein.

The invention claimed is:

1. A medical, surgical, or dental handpiece bearing assembly comprising:
   an outer ring defining an outer raceway and an inner ring defining an inner raceway; said inner and outer rings defining a radial distance between said inner and outer rings;
   a first shield proximate a first axial end of said bearing assembly and extending from one of said inner and outer rings towards the other of said inner and outer rings, wherein said first shield is integral with said outer ring;
   a second shield proximate a second axial end of said bearing assembly, wherein said second shield comprises a single-piece construction, said second shield elastically deformable to mechanically interlock with, and extend from one of said inner and outer rings towards the other of said inner and outer rings, said second shield composed of an engineering plastic comprised of an amorphous polyetherimide, and wherein said second shield can withstand exposure to temperatures of approximately 134 degrees Centigrade and exposure to steam without degradation of mechanical properties;
   wherein said first and second shields each have a length equal to at least 50% of the radial distance between said inner and outer rings;
   a plurality of balls between said inner and outer rings and positioned to contact said inner and outer raceways;
   a retainer positioned between said first and second rings defining a plurality of pockets which receives said balls, said retainer composed of an engineering plastic having a composition selected from either a poly(amide-imide) (PAI) or a polyetheretherketone (PEEK) to withstand repeated sterilization, autoclaving, and application temperatures without degradation of mechanical properties, said engineering plastic of said retainer includes carbon fillers and fluoropolymer particles, wherein said fluoropolymer is a polytetrafluoroethylene; and
   a lubricating grease disposed between the first shield and the second shield, adjacent to the plurality of balls, said grease having a viscosity of at least about 110 centistokes at approximately 104 degrees F.

2. The bearing assembly of claim 1 wherein said second shield is mounted to an inner diameter surface of said outer ring.

3. The bearing assembly of claim 1 wherein said second shield is mounted to an outer diameter surface of said outer ring.

4. The bearing assembly of claim 1 wherein said second shield is received on, and mechanically interlocked with, an axial surface of one of said inner and outer rings; said one of said inner and outer rings defining a groove which receives and interlocks with said second shield.

5. The bearing assembly of claim 4 wherein said second shield is mounted to an outer diameter surface of said inner ring, an inner diameter surface of said outer ring, or an outer diameter surface of said outer ring.

6. The medical, surgical, or dental handpiece bearing assembly of claim 5 wherein said second shield is mounted to an outer diameter surface of said outer ring.

7. The bearing assembly of claim 6 wherein at least said second shield is comprised of an engineering plastic having a 24 hour water absorption of approximately 0.25 per cent and has a heat deflection temperature of approximately 392 degrees F. at 264 psi.

8. The bearing assembly of claim 6 wherein said retainer is composed of an engineering plastic having a 24-hour water absorption of approximately 0.33 per cent and has a heat deflection temperature of approximately 436degrees F. at 264 psi.

9. The bearing assembly of claim 1 wherein said first shield and second shield extend substantially the full radial distance between said inner and outer rings.

10. The bearing assembly of claim 1 wherein the engineering plastic of said second shield is a material which remains as a barrier and preserves shield integrity at temperatures of approximately 134 degrees Centigrade and exposure to steam.

11. The bearing assembly of claim 1 wherein the thermal expansion properties of the engineering plastic of said second shield maintain a mechanical interlock at temperatures of approximately 134 degrees Centigrade and exposure to steam.

12. The bearing assembly of claim 1 wherein said engineering plastic of said second shield further includes glass filler.

13. The bearing assembly of claim 1 wherein said carbon fillers comprise graphite and/or carbon fibers.

14. The bearing assembly of claim 1 wherein the carbon is present in amounts greater than or equal to about 10 by weight %.

15. The bearing assembly of claim 1 wherein the fluoropolymer particles are present in amounts greater than or equal to about 1 by weight %.

16. The bearing assembly of claim 1 wherein the grease comprises a mineral base oil with polyurea thickener.

17. The bearing assembly of claim 1 wherein said plurality of balls are supported in an angular contact configuration.

18. The bearing assembly of claim 1 wherein one of said inner and outer rings has a relieved configuration; and
   wherein said retainer has a one-piece configuration fully encompassing the equator of each of said plurality of balls.

19. A medical, dental, or surgical handpiece containing a driven member, incorporating at least one bearing assembly of claim 1 to support said driven member.

20. The medical/dental handpiece of claim 19 wherein said handpiece comprises a head defining a cavity housing said driven member; said cavity including upper and lower recesses axially opposite said driven member, each of which receives one of said bearing assemblies; each of said bearing assemblies orientated in said recesses such that said second shield faces axially inward toward said driven member.

21. A medical, surgical, or dental handpiece bearing assembly comprising:
   an outer ring defining an outer raceway and an inner ring defining an inner raceway; said inner and outer rings defining a radial distance between said inner and outer rings;
   a first shield proximate a first axial end of said bearing assembly and extending from said outer ring towards said inner ring, wherein said first shield is integral with said outer ring;
   a second shield proximate a second axial end of said bearing assembly, wherein said second shield comprises a single-piece construction, elastically deformable to mechanically interlock with, and extend from, an outer diameter surface of said outer ring towards said inner ring, wherein said first shield and second shield extend substantially the full radial distance between said inner and outer rings;
   wherein at least said second shield is comprised of an engineering plastic, composite, or other material comprised of amorphous polyetherimide which can withstand exposure to temperatures of approximately 134 degrees Centigrade and exposure to steam without degradation of mechanical properties;
   a plurality of balls between said inner and outer rings and positioned to contact said inner and outer raceways;
   a retainer positioned between said first and second rings defining a plurality of pockets which receives said balls, said retainer composed of an engineering plastic having a composition selected from either a poly(amide-imide) (PAI) or a polyetheretherketone (PEEK) to withstand repeated sterilization, autoclaving, and application temperatures without degradation of mechanical properties, said engineering plastic of said retainer includes carbon fillers and fluoropolymer particles, wherein said fluoropolymer is a polytetrafluoroethylene; and
   a lubricating grease comprising a mineral base oil with polyurea thickener disposed between the first shield and the second shield, adjacent to the plurality of balls, said grease having a viscosity of at least about 110 centistokes at approximately 104 degrees F.

* * * * *